United States Patent [19]

Bolt et al.

[11] Patent Number: 4,635,653
[45] Date of Patent: Jan. 13, 1987

[54] SPARK PERFORATION OF WEB MATERIAL

[75] Inventors: Reginald C. Bolt; Derek H. Dyett; Robert E. Williams, all of High Wycombe, England

[73] Assignee: Molins PLC, London, England

[21] Appl. No.: 495,941

[22] Filed: May 19, 1983

[30] Foreign Application Priority Data

May 19, 1982 [GB] United Kingdom ............... 8214558

[51] Int. Cl.$^4$ .............................................. A24C 5/47
[52] U.S. Cl. ................................................... 131/281
[58] Field of Search .................... 131/281, 94, 95; 219/384

[56] References Cited

U.S. PATENT DOCUMENTS

| | | | |
|---|---|---|---|
| 4,121,595 | 10/1978 | Heitmann et al. | 131/281 |
| 4,219,727 | 8/1980 | Bolt | 219/384 |
| 4,377,172 | 3/1983 | Burger et al. | 131/202 |
| 4,390,032 | 6/1983 | Labbe et al. | 131/281 |
| 4,403,619 | 9/1983 | Dahlgrun | 131/281 |
| 4,447,708 | 5/1984 | Allen et al. | 131/281 |

Primary Examiner—V. Millin
Attorney, Agent, or Firm—Antonelli, Terry & Wands

[57] ABSTRACT

Filter cigarettes with a predetermined dilution factor are produced by perforating a filter attachment web by means of an adjustable perforating device prior to using portions of the web to join filters to cigarettes; measuring the porosity of the perforated web; measuring the dilution of cigarettes assembled with portions of the web; and controlling the perforating device by immediate response to the measured porosity and by progressive response to the dilution of the assembled cigarettes. The perforating device may comprise spark perforating electrodes, the web being possibly passed twice between the electrodes. In particular, the perforating device includes a number of pairs of electrodes defining spark gaps therebetween and lying along a line inclined to the direction of movement of the web. Individual rod electrodes are located between and spaced from opposed metal plates connected to a power supply to form capacitances in series with the spark gaps.

22 Claims, 8 Drawing Figures

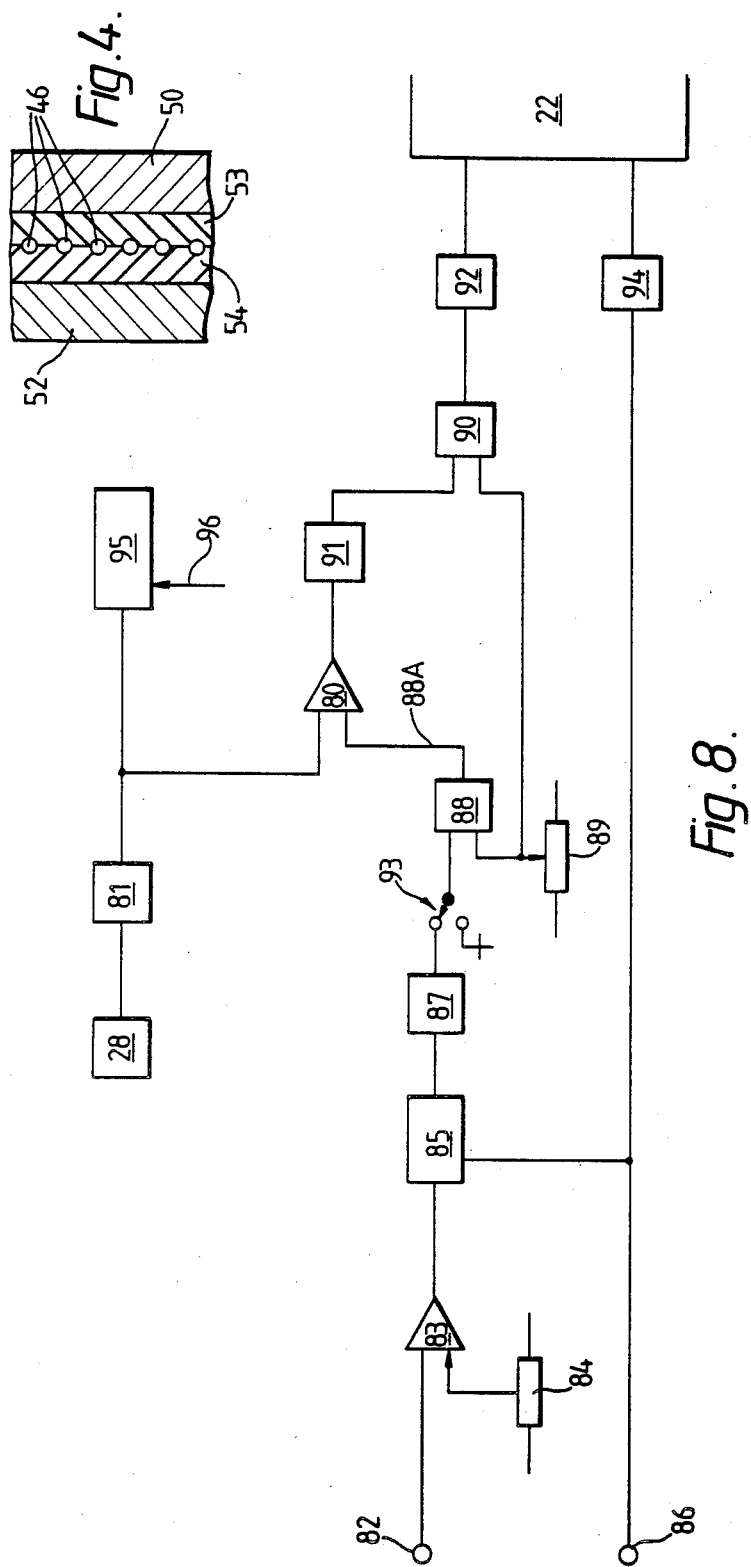

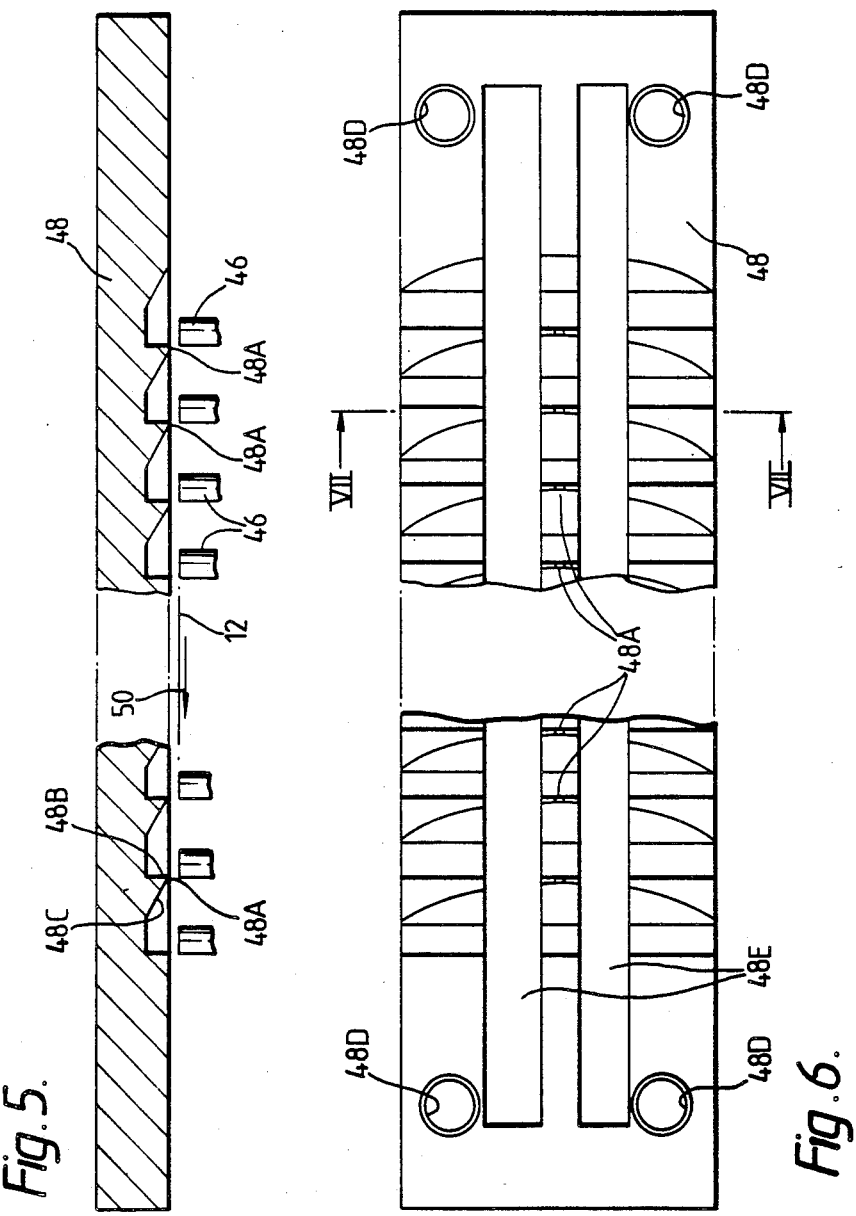

SPARK PERFORATION OF WEB MATERIAL

This invention is concerned with a number of improvements in relation to perforation of a moving web, especially by means of sparking and especially with reference to perforation of the paper web material used for filter attachment in a filter cigarette making machine. The various improvements may be used independently or in any desired combination.

According to a first aspect of this invention there is provided a method of producing cigarettes with a predetermined dilution factor comprising perforating a filter attachment web by means of an adjustable perforating device prior to using portions of the web to join filters to cigarettes; measuring the porosity of the perforated web; measuring the dilution of cigarettes assembled with portions of the web; and controlling the perforating device by immediate response to the measured porosity and by progressive response to the dilution of the assembled cigarettes. The dilution signal is obtained from a cigarette inspection device which measures the dilution of each cigarette produced; for example, the inspection device may be as described in U.S. Pat. No. 4,325,350. A running average of the dilution signal may be used to control the perforating device, For example, it may be obtained by means of an analogue integrating device or it may be established digitally from a predetermined number of previously tested cigarettes.

It is important that a progressive control in response to dilution or mean dilution is achieved. That is to say, there is no abrupt change in the control applied to the perforating device. Instead a change in either direction is effected at a predetermined measured rate, either stepwise or continuously. In apparatus terms this preferably involves the use of an up/down counter as described below.

In a preferred arrangement the perforating device is controlled in response to the difference between the measured porosity and a porosity reference signal, and the reference signal is proressively compensated for changes in cigarette dilution.

According to a second aspect of the present invention there is provided an apparatus for producing filter cigarettes with a predetermined dilution factor, comprising an adjustable perforating device for perforating a filter attachment web; means for measuring the porosity of the perforated web; means for using portions of the perforated web to join filters to cigarette rods to form filter cigarettes; means for measuring the dilution of the filter cigarettes; and control means for controlling the perforating device immediately in response to the measured porosity and progressively in response to dilution measurement of the filter cigarettes.

According to a third aspect of the present invention there is provided a method of spark perforating a filter attachment web, comprising passing a web between two electrodes first in one direction and then in the opposite direction, the electrodes being connected to a power supply so that sparks pass through the web while the web is moving in both directions between the electrodes.

Preferably the web has a printed surface which faces one electrode during the first pass and the other electrode during the second pass.

According to a fourth aspect of the present invention there is provided an apparatus for spark perforating a filter attachment web, comprising spaced electrodes connected to a power supply for producing sparks between the electrodes; and means for passing a web between the electrodes first in one direction and then in the opposite direction so that said sparks pass through the web during both passes of the web between the electrodes.

According to a fifth aspect of the present invention there is provided an apparatus for spark perforating a moving web, especially a filter attachment web, comprising a number of pairs of electrodes lying along a line inclined to the direction of movement of the web, the electrodes on one side of the web comprising individual rods which are held between metal plates which are connected to a power supply and together with the electrode rods form capacitances which are in series with the circuits including the spark gaps between the respective electrode pairs, and including dielectric material in the space between the plates and the rods by which the rods are located in position between the plates.

The invention will now be described, by way of example, with reference to the accmpanying drawings, of which:

FIG. 4 is a section on the line IV—IV in FIG. 3;

FIG. 5 is a longitudinal section, on a larger scale, of one of the upper electrodes shown in FIG. 3;

FIG. 6 is a view from underneath the electrodes shown in FIG. 5;

FIG. 7 is a section on the line VII—VII in FIG. 6 and

FIG. 8 is a block diagram showing a control circuit which may be used in the system shown in FIG. 1.

Figure 1:
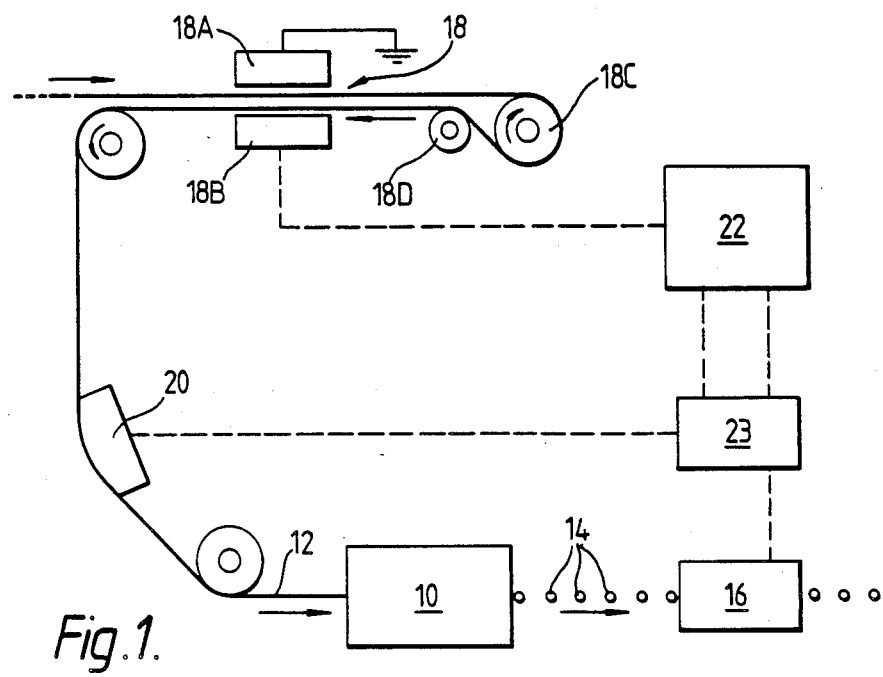
FIG. 1 is a diagrammatic illustration of a complete machine including a web perforator, a porosity measuring assembly and a cigarette dilution testing device.

FIG. 1 shows a filter attachment machine including an assembly device 10 whereby portions cut from a web 12 are wrapped around abutting cigarette and filter portions, in any well-known way, to produce filter cigarettes 14. A cigarette inspection device 16 tests each cigarette in turn to detect cigarettes with faults, and also measures the dilution factor of each cigarette or the average dilution over a number of successive cigarettes.

On its way to the filter attachment device 10, the web 12 passes a spark perforating device 18 and a porosity measuring assembly 20. The perforating device 18 is powered by a power unit 22 controlled by a control circuit 23 in response to signals received from the porosity measuring assembly 20 and the inspection device 16. This provides two perforation zones across the width of the web 12. A possible arrangement for the control circuit 23 is shown diagrammatically in FIG. 8.

The perforating device 18 includes upper and lower members 18A and 18B carrying electrodes between which sparks are now produced to perforate the web; the electrodes of the lower member 18B are live, the voltage and/or the frequency of the power supply from the power unit 22 being controlled by the control circuit 23. The electrodes of the upper member 18A are earthed as shown.

Figure 3:
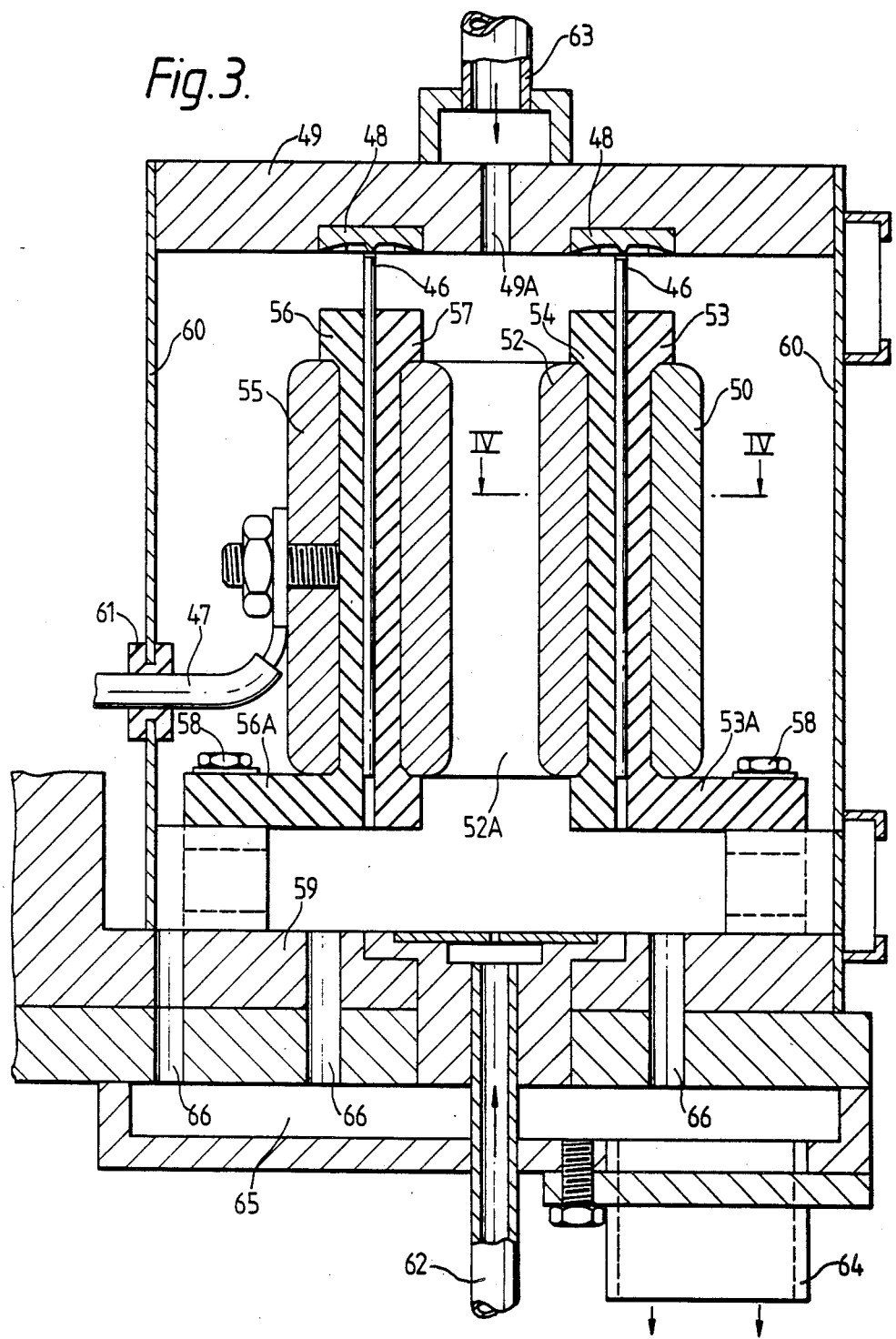
FIG. 3 is a sectional view of the perforator in a plane transverse to the direction of movement of the web.

The web is arranged to make two passes between the upper and lower sets of electrodes. As shown in FIG. 1, the web first moves to the right, then returns around a pulley 18C before being guided by a further pulley 18D into a path parallel and close to the upper pass of the web; the web makes a second pass between the electrodes while moving to the left. In the case of filter attachment paper having a print on one side (e.g. of cork-like appearance as is common), the print preferably lies on the surfaces of the web which face outwards towards the respective electrodes. That facilitates removal of debris created by the print, for example by means of a purging air flow through the perforator, which may be as shown in FIG. 3.

Figure 2:
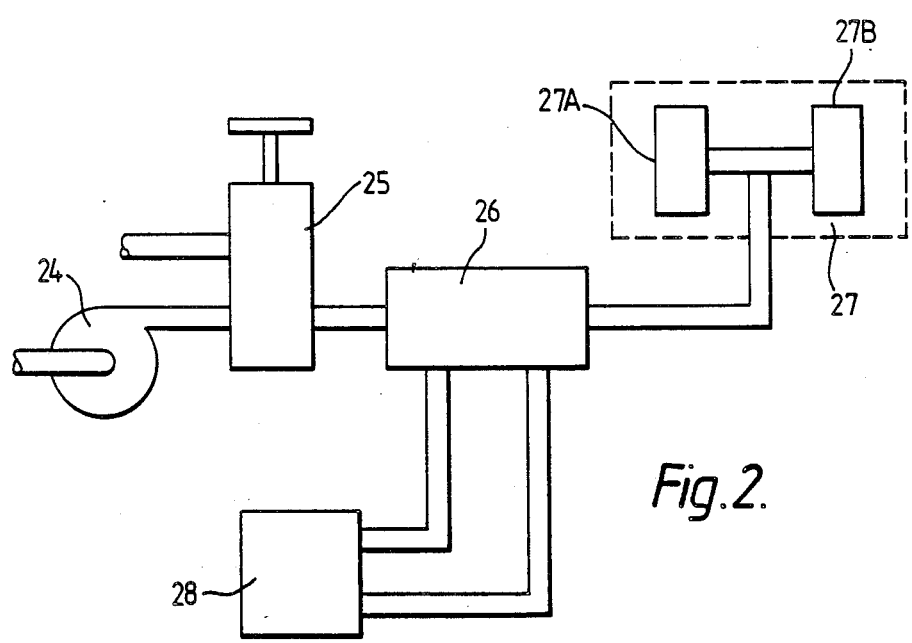
FIG. 2 is a diagrammatic illustration of the porosity measuring assembly.

FIG. 2 illustrates diagrammatically a possible arrangement for the porosity measuring assembly 20. A fan 24 supplies air via a pressure regulator 25 and a laminar flow orifice 26 to a measuring head 27. Tension is maintained in the web 12 to urge the web firmly into sealing contact with the head 27 so that air is forced through the web at both perforation zones which move respectively across air outlet ports 27A and 27B. The pressure regulator (for example, a Fairchild Precision Regulator, Kendall model 10, part No. 10112TL) provides a regulated pressure of 10 cm W.G. and the resulting flow is indicative of the porosity of the web. Flow is monitored by measuring the pressure drop across orifice 26 by means of a differential pressure transducer 28. (A suitable laminar flow orifice is the FC093-6 model, and a suitable transducer is the FC040/5 mm W.G., both devices being supplied by Furness Controls Limited.)

Since this system works by blowing air through the perforations (rather than using suction) it ensures that loose material left on the paper by the perforation process is blown away and cannot enter and contaminate the laminar flow orifice in particular.

FIGS. 3 to 6 show a spark perforating device which may be used in the system shown in FIG. 1. This device incorporates an improvement to an invention described in British patent application No. 2079212.

As shown in FIGS. 3 to 5, the perforator includes a row of rod electrodes 46 for each of the two perforation zones. These electrodes are connected (in a manner described below) to a high tension lead 47. Upper electrodes 48 are mounted in an earthed carrier member 49, each of these electrodes 48 being in the form of a metal bar machined so as to provide points 48A as described below. The detailed construction of each of the electrodes 48 is shown in FIGS. 5 to 7.

Each of the rod electrodes 46 cooperates with a point 48A on a corresponding upper electrode, their relative dispositions being shown in FIG. 5. It should be noted that each rod electrode 46 is offset with respect to the portion of the corresponding electrode 48 which defines the point 48A, which lies closest to the rod electrode. More specifically, as shown in FIG. 5, the closest path for each spark between the electrodes extends between a point 48A and one edge of the corresponding rod electorode 46, namely the edge lying upstream in relation to the direction of movement of the paper web (indicated by the arrow 50). The clearance between the electrodes 46 and 48 may, for example be 0.25 mm. As an idea of scale, the rod electrodes 46 may have a diameter of 2.3 mm (pitch 6 mm).

The shape of each member 48 forming the upper electrodes is shown in FIGS. 5 to 7. It is important to note that each member 48 is machined to produce a row of saw-tooth shaped projections extending downwards from a body of substantial mass which carries away heat generated by the sparking. Reference has been made to the points 48A, but it should be noted that these points are in fact flat lands of small dimension as shown particularly in FIG. 6. Each "point" lies at the lower extremity of a projection having a vertical flank 48B which is aligned with the downstream side of the corresponding rod electrode 46, and a sloping flank 48C which diverges away from the web in the direction of movement thereof.

Each vertical flank 48B lies in a vertical plane transverse to the direction of movement of the web, the closest portions of the cooperating electrodes being in that plane; the rod electrode lies entirely upstream of that plane, while the projection forming the effective electrode portion of the bar 48 lies on the other side of the plane (i.e. downstream in relation to the direction of movement of the web.

Each member 48 lies in a groove in the carrier member 49 and is secured thereto by bolts (not shown) passing through apertures 48D.

The perforator is set with the rows of electrodes inclined to the direction of movement of the web by an adjustable small angle. Thus the respective pairs of cooperating electrodes form separate rows of longitudinal perforations in the web which are slightly spaced laterally across the web.

Each of the rod electrodes 46 is connected to the high tension cable 47 via a series capacitance formed in the following way. As shown particularly in FIG. 4, the rod electrodes 46 of one row lie between a metal plate 50 and a metal body 52. Between those metal members and the electrodes there are two ceramic plate-like parts 53 and 54 which are machined with grooves of semi-circular cross-section to receive the electrodes 46, as shown in FIG. 4. The member 52 is formed with a vertical slot 52A; its left-hand side portion cooperates with a further metal plate 55 to sandwich between them a pair of ceramic members 56 and 57 which are similar to the members 53 and 54. The metal parts 50, 52 and 55 are electically connected together at their ends by horizontal metal straps (not shown) which lie across the ends of those members and are secured to the members by bolts, thus securing together the entire assembly.

It will be understood that the ceramic parts provide a dielectric between the metal members and the electrodes. As a result, there is a current-limiting capacitance between the high tension lead 47 and each of the electrodes 46. This ensures that substantially the same current (from the sparking) flows between each electrode member 48 and each of its cooperating rod electrodes 46.

There may be a thin layer of silicon rubber or ceramic adhesive between each of the ceramic parts and the adjacent metal parts and electrodes 46.

The ceramic parts 53 and 56 have flanges 53A and 56A whereby the lower electrode assembly is secured in an insulating manner, by means of Nylon bolts 58, to a metal base member 59 which is earthed (in a manner not shown). The carrier 49 for the upper electrodes 48 is electrically connected to the base member 59 via a metal case 60. The cable 47 passes through an aperture in the case including an insulating bush 61.

Air is drawn through the perforator to carry away gas and other debris produced by spark erosion of the web. In the specific arrangement shown in FIG. 3 (which may however readily be varied) air from a source of compressed air is blown into the enclosure of the perforator via pipes 62 and 63, while an air mover 64 is arranged to extract air from the enclosure via a manifold 65 and a number of vertical passages 66 extending through the base 59. The air mover may be of any known construction and may produce movement of air through a venturi action produced by compressed air blown into the air mover in a well-known manner.

With reference to FIG. 6, each electrode member 48 and the parts of the member 49 lying between each member and a row of air supply slots 49A may be machined away to the level shown by the dotted line (i.e. flush with the bottoms of longitudinal grooves 48E) to allow air from the slots 48A to pass freely over the top of the paper 12, between the tooth-like projections 48B, 48C to cary away debris.

Instead of the single air mover (64) for exhausting air from the perforator enclosure, there may be for example be two air movers mounted respectively in the opposite case members 60.

The flow of air around the electrodes, for cooling and removing debris may be improved by providing vertical passages between adjacent projections of the upper electrode 48 and supplying air pressure to these passages via a pressure slot formed in the carrier member 49. In addition, suction may be applied below and to the sides of the upper electrodes 48 (as viewed in FIG. 3) by holes in the carrier member 49 supplied via a suction manifold placed above the carrier. This suction may also be used to urge the paper towards the upper electrodes, and the arrangement then preferably includes guides to limit upward movement of the web to avoid actual contact between the web and the upper electrodes or to minimise the force with which any such contact is made.

To avoid the risk of damaging the paper, and to reduce electrode wear, the projections may terminate in a flat surface perpendicular to the vertical flank 48B. The corner thus formed by said surface and said flank forms a point from which sparks may cross the gap. The upper electrode 48 and rod electrodes 46 are therefore brought closer together to provide a gap of suitable width. The upper electrodes may be of mild steel, preferably with a coating of Rhodium. The rod electrodes are preferably of nickel chromium alloy.

FIG. 8 shows a possible arrangement for the control circuit 23 in FIG. 1. The output from the transducer 28 (indicative of web porosity) is applied to a comparator 80 via a variable gain until 81 (e.g. a potentiometer or variable-gain amplifier). At the comparator 80 the attenuated (or amplified) porosity signal is compared with a controlled reference signal, obtained as described below.

A cigarette inspection device (not shown) provides an output to a terminal 82 and thence to a comparator 83 indicative of the dilution of the cigarette then passing through the inspection device or of the average dilution of a predetermined number of previously measured cigarettes. At the comparator 83 the dilution signal is compared with a pre-selected dilution reference from a potentiometer 84, which reference corresponds to the desired dilution level.

If the dilution or average dilution as measured by the cigarette inspection device is lower than the dilution reference, the output from the comparator 83 goes high. The output from the comparator 83 is applied to an up-down counter 85 which receives clock pulses from the machine via a terminal 86 at a rate of one pulse per cigarette or per two cigarettes produced by the machine. When the output from the comparator 83 is high, the up/down counter 85 counts up on receiving a clock pulse. Likewise when the output from the comparator 83 is low the up/down counter 85 counts down on receiving a clock pulse.

The output from the up/down counter 85 is applied to a digital-to-analogue converter 87 which produces an analogue output at a level proportional to the count level reached by the counter. The controlled reference signal for the comparator 80, transmitted along the line 88A, is produced by adding the output of the analogue-to-digital converter 87 to a porosity reference signal by means of a summing amplifier 88; the porosity reference signal is obtained from a potentiometer 89.

The output from the comparator 80 is applied to a summing amplifier 90 via a low pass filter 91. The summing amplifier 90 also receives the porosity reference signal from the potentiometer 89. The output from the summing amplifier 90 is applied to the perforator power unit 22, via an opto-isolater 92, and controls the power supplied to the perforator and hence the rate at which material is removed from the filter tipping web by the perforator.

The variable gain unit 81 is pre-set so that the system reaches a steady state condition at the desired porosity level. In this condition the output from the comparator 80 will tend to fluctuate between high and low output levels. This fluctuating signal is smoothed out by the low pass filter 91 so that an analogue signal is applied to the summing amplifier 90 at a level related to the average output of the comparator 80. The combinationof the up/down counter 85 and the digital-to-analogue converter 87 provides a delay in the dilution control loop. This is required to stabilise the system because of the long delay between perforating a portion of web and testing the dilution of a cigarette assembled with that portion of the web, which may correspond approximately to the time it takes for 200 cigarettes to be made. The counter also retains the average dilution value if the machine stops running. If required, the delay may be increased by increasing the resolution of the up/down counter or by reducing the clock pulse frequency by means of a frequency divider.

As stated above, in normal operation the output level of the comparator 80 will fluctuate, thus requiring a low pass filter to produce a stable analogue signal. An alternative approach is to use two comparators, one being arranged to respond when the porosity signal goes above an upper reference, and the second being arranged to respond when the porosity signal goes below a lower reference. When the porosity signal is outside the range lying between these two references an up/-down counter may be arranged to count in the required direction and in turn supply a digital-to-analogue converter as before. When the porosity signal lies within that range the clock pulses applied to the up/down counter may be suppressed, thus holding the analogue signal supplied to the perforation control unit steady.

A possible variation to the system detailed in FIG. 8 is to supply the porosity reference signal, the delayed average dilution signal and the measured porosity signal to a single summing amplifier. The output from such an amplifier may then be compared with a preset reference level by means of a comparator.

As shown in FIG. 8, the circuit may function without dilution control when desired by moving a switch 93 to the lower position. The perforation control unit 22 is also arranged to receive clock pulses from the machine via an opto-isolator 94.

The output from the variable gain unit is also applied to a porosity display device 95 which is arranged to sample said output on receiving a clock pulse from terminal 86 via a line 96. The display device 95 may be arranged to average a number of readings, thus giving an indication of average porosity, and is arranged to maintain an output when the machine is not actually running.

What we claim is:

1. A method of producing filter cigarettes with a predetermined dilution factor, comprising perforating a filter attachment web by means of an adjustable perforating device prior to using portions of the web to join filters to cigarettes; measuring the porosity of the perforated web; measuring the dilution of cigarettes assembled with portions of the web; and controlling the perforating device by immediate response to the measured porosity and by progressive response to the dilution of the assembled cigarettes, the perforating device being controlled in response to the measured porosity, and the porosity reference being progressively compensated for changes in cigarette dilution.

2. A method according to claim 1 in which changes in the cigarette dilution signal are transmitted via an up/down counter to produce a progressively changing signal for controlling the perforating device.

3. A method of producing filter cigarettes with a predetermined dilution factor, comprising perforating a filter attachement web by means to join filters to cigarettes; measuring the porosity of the perforated web; measuring the dilution of cigarettes assembled with portions of the web; and controlling the perforating device by immediate response to the measured porosity and by progressive response to the dilution of the assembled cigarettes, changes in the cigarette dilution signal being transmitted by an up-down counter to produce a pregressively changing signal for controlling the perforating device.

4. A method according to claim 3 in which the perforating device is controlled in response to the difference between the measured porosity and a porosity reference signal, and the reference signal is progressively compensated for changes in cigarette dilution.

5. A method of spark perforating a filter attachment web, comprising passing a web between two electrodes first in one direction and then in the opposite direction, the electrodes being connected to a power supply so that sparks pass through the web while the web is moving in both directions between the electrodes.

6. A method according to claim 5 in which the web has a printed surface which faces one electrode during the first pass and the other electrode during the second pass.

7. Apparatus for producing filter cigarettes with a predetermined dilution factor, comprising an adjustable perforating device for perforating a filter attachment web; means for measuring the porosity of the perforated web; means for using portions of the perforated web to join filters to cigarette rods to form filter cigarettes; and control means for controlling the perforating device immediately in response to the measured porosity and progressively in response to said measured dilution, and control means including means for comparing said measured porosity with a reference signal to produce a control signal which controls said perforating device, and means for progressively compensating the reference signal for changes in said measured dilution.

8. Apparatus according the claim 7 in which the control means includes an up/down counter which counts up or down in response to a signal indicative of said measured dilution so as to produce a progressively changing output; and a digital-to-analogue converter for converting the output of the counter.

9. Apparatus for producing filter cigarettes with a predetermined dilution factor, comprising an adjustable perforating device for perforating a filter attachment web; means for measuring the porosity of the perforated web; means for using portions of the perforated web to join filtes to cigarette rods to form filter cigarettes; and control means for controlling the perforating device immediately in response to the measured porosity and proressively in response to said measured dilution, said control means including an up/down counter, which counts up or down in response to a signal indicative of said measured dilution so as to produce a progressively changing output, and a digital-to-analog converter for converting the output of the counter.

10. Apparatus according to claim 9 in which a control signal from the control means is applied to the perforating device via a low pass filter.

11. Apparatus acording to claim 9 in which the control means includes means for comparing said measured porosity with a reference signal to produce a control signal which controls said perforating device; and means for progressively compensating the reference signal for changes in said measured dilution.

12. Apparatus according to claim 9 in which the up/down counter counts in response to clock pulses having a frequency related to the rate of production of cigarettes.

13. Apparatus according to claim 12 in which the up/down counter receivs clock pulses via a frequency divider.

14. Apparatus according to claim 9 in which the said up/down counter or another up/down counter included in the control means is arranged to cease counting when the dilution signal lies within predetermined limits.

15. Apparatus for producing cigarettes with a predetermined dilution factor, comprising an adjustable perforating device for perforating a filter attachment web; means for measuring the porosity of said web and producing a porosity signal indicative of said measurement; means for using portions of said perforated web to join filters to cigarette rods to form filter cigarettes; means for measuring the dilution of said filter cigarettes and producing a dilution signal; an up/down counter arranged to count up or down in response to said dilution signal so as to produce a progressively changing output; a digital-to-analogue converter arranged to convert the output of said counter; means for producing a control signal for control of the perforating device from the output of the converter combined with the porosity signal and with a manually controllable dilution reference.

16. Apparatus for spark perforating a moving web, especially a filter attachment web, comprising spaced electrodes connected to a power supply for producing sparks between the electrodes; and means for passing a web between the electrodes first in one direction and then in the opposite direction so that said sparks pass through the web during both passes of the web between the electrodes.

17. Apparatus according to claim 16 in which the dielectric material is in the form of plates of ceramic material between which the rods are secured.

18. Apparatus according to claim 17 in which said grounded electrodes comprise projections on a common metal bar.

19. Apparatus according to claim 16 in which the metal plates are connected to a high tension supply and in which the electrodes cooperating with the rod electrodes are grounded.

20. Apparatus according to claims 19 in which said grounded electrodes are formed as pointed saw-tooth shaped projections, said rod electrodes having substantially flat ends substantially parallel to the plane of said web during use.

21. Apparatus according to claim 16 in which each pair of cooperated electrodes has its closest portions lying substantially in a plane transverse to the direction of movement of the web, one electrode extending substantially to one side of the plane and the other electrode extending substantially to the other side of the plane.

22. Apparatus for spark perforating a moving web, especially a filter attachment web, comprising a number of pairs of electrodes defining spark gaps therebetween and lying along a line inclined to the direction of movement of the web, the electrodes on one side of the web comprising individual rods located between and spaced from opposed metal plates which are connected to a power supply thus forming capacitances in series with said spark gaps, and including dielectric material in the space between said plates and said rods by which said rods are located in position between said plates.

* * * * *